United States Patent
Kubitza et al.

(10) Patent No.: US 9,500,885 B2
(45) Date of Patent: Nov. 22, 2016

(54) METHOD AND APPARATUS FOR DETERMINING THE HABITUAL HEAD POSTURE

(75) Inventors: Matthias Kubitza, Aalen (DE); Michael Gamperling, Leipheim (DE); Jesús-Miguel Cabeza-Guillén, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 639 days.

(21) Appl. No.: 13/329,043

(22) Filed: Dec. 16, 2011

(65) Prior Publication Data

US 2012/0182521 A1 Jul. 19, 2012

Related U.S. Application Data

(63) Continuation of application No. PCT/EP2010/002821, filed on May 8, 2010.

(30) Foreign Application Priority Data

Jun. 17, 2009 (DE) ........................ 10 2009 025 215

(51) Int. Cl.
  *G02C 13/00* (2006.01)
  *A61B 3/10* (2006.01)
  *G02C 7/02* (2006.01)

(52) U.S. Cl.
  CPC .............. *G02C 13/005* (2013.01); *A61B 3/10* (2013.01); *G02C 7/025* (2013.01)

(58) Field of Classification Search
  CPC .............. A61B 5/11; A61B 3/10; G02C 13/00
  USPC ..................................... 33/512; 351/204, 246
  See application file for complete search history.

(56) References Cited

U.S. PATENT DOCUMENTS

| | | | | |
|---|---|---|---|---|
| 4,310,225 A | * | 1/1982 | Davis | ....................... 351/159.52 |
| 6,659,609 B2 | * | 12/2003 | Mothes | .......................... 351/204 |
| 6,827,443 B2 | | 12/2004 | Fisher et al. | |
| 6,849,050 B1 | * | 2/2005 | Russo | .................... A61B 3/024 |
| | | | | 600/558 |
| 7,384,144 B2 | | 6/2008 | Ross-Messemer et al. | |
| 7,540,612 B2 | | 6/2009 | Fischer | |

(Continued)

FOREIGN PATENT DOCUMENTS

| DE | 299 10 680 U1 | 10/1999 |
|---|---|---|
| DE | 10 2004 063 160 A1 | 7/2006 |

(Continued)

OTHER PUBLICATIONS

Translation of international preliminary report on patentability dated Jan. 5, 2012 of international application PCT/EP2010/002821 on which this application is based.

(Continued)

*Primary Examiner* — R. A. Smith
(74) *Attorney, Agent, or Firm* — Walter Ottesen, P.A.

(57) ABSTRACT

A method for determining the habitual head posture of a subject includes recording the head posture over a period of time and determining a preferred head posture from the recording. Also, an apparatus (100) for determining the habitual head posture of a subject includes a recording device (110) for recording the head posture over a period of time and a determining device (112, 114) for determining a preferred head posture from the recording.

28 Claims, 2 Drawing Sheets

(56) References Cited

U.S. PATENT DOCUMENTS

| | | |
|---|---|---|
| 7,588,335 B2 | 9/2009 | Kubitza |
| 8,506,078 B2 * | 8/2013 | Chauveau et al. ............ 351/200 |
| 8,562,134 B2 * | 10/2013 | Wada ............................ 351/204 |
| 8,851,678 B2 * | 10/2014 | Pelah ................... A61B 3/0041 351/224 |
| 9,033,496 B2 * | 5/2015 | Divo .................... G02C 13/005 351/204 |
| 2003/0143391 A1 | 7/2003 | Lai |
| 2007/0229761 A1 | 10/2007 | Gimenez Carol et al. |
| 2009/0040460 A1 * | 2/2009 | Bonnin .................. A61B 3/113 351/209 |
| 2009/0207375 A1 | 8/2009 | Fischer |
| 2009/0214086 A1 | 8/2009 | Thomet |
| 2010/0149486 A1 | 6/2010 | Sayag |
| 2010/0195046 A1 * | 8/2010 | Blum et al. .................... 351/204 |
| 2012/0010533 A1 * | 1/2012 | Arnett et al. ................. 600/590 |
| 2012/0154751 A1 * | 6/2012 | Pelah ................... A61B 3/0041 351/224 |

FOREIGN PATENT DOCUMENTS

| | | |
|---|---|---|
| DE | 10 2008 018 198 A1 | 10/2009 |
| EP | 0 898 930 A2 | 3/1999 |
| EP | 1 591 064 A1 | 11/2005 |

OTHER PUBLICATIONS

International Search Report dated Sep. 30, 2010 of international application PCT/EP 2010/002821 on which this application is based.

Translation of examination request of German Patent Office dated Nov. 30, 2009 of German patent application 10 2009 025 215.0 on which this application is based.

English translation and Office action of Chinese Patent Office dated Nov. 21, 2012 of corresponding Chinese patent application 201080027200.6.

English translation of Office action of Chinese Patent Office dated Jul. 16, 2013 of corresponding Chinese patent application 201080027200.6.

English translation and Office action of German Patent Office dated May 27, 2014 of German patent application 10 2009 025 215.0 on which this application is based.

Office action of Canadian Patent Office dated Aug. 26, 2014 of corresponding Canadian patent application 2,768,317.

Office action of Canadian Patent Office dated Oct. 16, 2015 of corresponding Canadian patent application 2,768,317.

* cited by examiner

METHOD AND APPARATUS FOR DETERMINING THE HABITUAL HEAD POSTURE

CROSS REFERENCE TO RELATED APPLICATIONS

This application is a continuation application of international patent application PCT/EP 2010/002821, filed May 8, 2010, designating the United States and claiming priority from German application 10 2009 025 215.0, filed Jun. 17, 2009, and the entire content of both applications is incorporated herein by reference.

FIELD OF THE INVENTION

The invention relates to a method for determining the habitual head posture of a subject and to an apparatus for determining the habitual head posture of a subject. Furthermore, the invention also relates to a method for determining centering data and to an apparatus for determining centering data. The invention also relates to a computer program for carrying out the methods referred to above.

BACKGROUND OF THE INVENTION

When opticians, for optically adapting spectacles, determine the centering data, that is, all required information for the correct centering of spectacle lenses in a spectacle frame for the individual use purpose of the customer or subject, then the following procedure can be adopted:

The customer is requested to adopt a head and body posture that is as natural as possible. The centering values are then defined by marking the viewing points in the disc plane of the spectacle frame by means of a pen or by means of video recording and subsequent manual centering data determination (such as in the case of the video centering device sold by the applicant under the trade name "Video Infral") or automated centering data determination (such as in the case of the video centering device sold by the applicant under the trade name "RV terminal").

In order to determine the forward inclination angle, an aid called "Y-Stick" is known, which "freezes" the forward inclination angle of the spectacle frame at a point in time in order that the angle can subsequently be read. The forward inclination angle thus detected is used in a subsequent step for positioning the customer in the same position in front of a centering system.

Furthermore, EP 1 591 064 A1 discloses a measuring instrument for determining the inclination of the head, this being sold by the applicant of EP 1 591 064 under the designation "Ysis". The measuring instrument is fixed to the spectacle frame. This proposal aims to capture the "normal" head posture at a point in time in each case for the near and far viewing directions. From the head inclinations assumed when looking into the distance and when reading, the difference in head inclination between distant-vision and close-vision tasks is determined. The associated viewing points through the spectacle lens are then determined therefrom.

All the above methods are static, that is to say that a "snapshot" of the respective situation is used for determining a habitual head posture.

U.S. Pat. No. 6,827,443 discloses classifying the behavior of a wearer of spectacles with regard to the latter's viewing habits. The typical head and eye movement is determined for various vision tasks. Depending on that, the viewing behavior of the subject is categorized according to "mobility" of the eyes and of the head ("head/eye mover"). The results of the analysis are used in this case as a basis for selecting a suitable spectacle lens.

United States patent application publication 2007/0229761 discloses ascertaining the most frequent viewing directions relative to the head. For this purpose, head posture and viewing direction are detected simultaneously. The relative "net" viewing direction and the resultant viewing point through a spectacle lens are determined from the relative viewing directions determined.

DE 10 2004 063 160 A1 describes a method and a device for adapting spectacles, in particular for detecting the habitual head posture of a subject, the measurement data of which are incorporated in video centering data determination. The method involves taking a number of video photographs of the subject in order to determine the head posture angles of a subject in various head posture positions, detecting the head posture angles and adjusting them with the forward inclination angle of the spectacle frame and also the corneal vertex distance. The corresponding video photographs are captured at a moment when, in the operator's opinion, the subject has adopted his or her natural habitual head posture.

A centering measurement, that is, a measurement which involves determining all the required information for the correct centering of spectacle lenses in a spectacle frame for the individual use purpose of the customer or subject, constitutes a forced situation for the customer of the optician. Although it is known from the centering measurement how the customer holds his or her head during a recording, this head posture does not necessarily correspond to the "normal", that is, the most frequent head posture in actually unforced situations.

This also does not change if the method described in DE 10 2004 063 160 A1 is used. Furthermore, this method entails the risk of the purportedly natural head posture not being recorded at all, but rather a different head posture, since the subject has already adopted a different head posture within the reaction time of the operator.

SUMMARY OF THE INVENTION

It is an object of the invention to provide an improved method for determining the habitual head posture of a subject, to be precise in such a way that the head posture determined comes closer to the actual "normal" head posture of the subject than is the case for the above-described methods concerning the prior art. A further object of the invention is to provide a corresponding apparatus for more precisely determining the habitual head posture of a subject. Furthermore, the object of the invention consists in providing a method rendered more precise for centering data determination and a corresponding apparatus suitable for performing the method according to the invention.

The method according to the invention for determining the habitual head posture of a subject comprises the following method steps:

a. recording the head posture over a certain period of time; and,    b. determining a preferred head posture from the recorded head posture.

The corresponding apparatus for determining the habitual head posture of the subject correspondingly comprises:

a. a recording device for recording the head posture over the period of time; and, b. a determining device for determining the preferred head posture from the recorded head posture.

The method outlined above and the corresponding apparatus designed, in particular, for carrying out this method prevent the habitual head posture of the subject from being mistakenly assumed as a head posture which is recorded or determined randomly at a point in time and which precisely does not correspond to the subject's usual head posture, as can be the case according to the methods from the prior art described in the introductory part of the disclosure under the heading "Background of the Invention". The objects presented are therefore achieved in their entirety by this method and the corresponding apparatus.

The assumption of the habitual head posture as the preferred head posture determined from a head posture recorded over a certain time also makes it possible, for example, to correct the head posture measured during the centering measurement (for example, with the aid of the video centering devices sold by the applicant under the designations Relaxed Vision Terminal and Video Infral), such that the centering data are determined on the basis of the "normal" rather than random head posture.

The invention therefore also encompasses a method for determining centering data, wherein:
a. an actual instantaneous head posture of a subject is determined;
b. an arrangement of a spectacle frame relative to the actual instantaneous head posture determined is determined;
c. a habitual head posture determined by an automated method is determined; and,
d. the actual instantaneous head posture determined is corrected with the aid of the habitual head posture determined in an automated manner.

The invention correspondingly also relates to an apparatus for determining centering data and includes:
a. a head posture determining device for determining the actual instantaneous head posture of the subject;
b. a determining device for determining the arrangement of the spectacle frame relative to the actual instantaneous head posture determined;
c. an apparatus for determining the habitual head posture in an automated manner; and,
d. a correction device for correcting the actual instantaneous head posture determined with the aid of the habitual head posture determined.

The object specified above is achieved in its entirety by such a method and the corresponding apparatus.

In the method according to the invention for determining the habitual head posture of a subject, the period of time within which the head posture is recorded can be predetermined. Thus, by way of example, the head posture can be recorded only during the time during which reliable data on the habitual posture of the subject's head can actually be inferred. The recording of forced and/or unnatural head postures can be avoided. Furthermore, the period of time can be defined individually such that the data material recorded permits a sufficiently reliable statement about the actual habitual head posture. It is expedient, for example, if, from the recording, only those time segments within which the subject has actually adopted a head and/or body posture corresponding to ergonomic principles are selected for the purpose of determining the habitual head posture.

The preferred head posture should be understood to mean the head posture in which the subject keeps their head during a predetermined vision task with a certain probability. Typical values for the probability are, for example, above 30%, above 50%, above 80% or even above 90% for the specific vision task. Such an analysis can be carried out by means of customary mathematical/statistical methods. Suitable software algorithms can, as necessary automatically or with support by the user, eliminate extreme values (outliers) from the recorded volume of data of the habitual head posture, before a typical head posture is determined. By way of example, a selection is then made from the set of these most probable head postures.

The recorded head posture in which the subject keeps their head with the highest probability can also be selected as the preferred head posture.

Although it is possible, in principle, to leave it to the discretion of the subject in what body posture and/or what the subject views during the recording of their head posture, it is expedient in many cases to impose specific vision tasks on the subject. Particularly if the head posture is incorporated into the spectacle lens calculation or the centering of a spectacle lens, it is expedient to devote particular attention to the viewing directions for the near range and/or the far range. The invention provides, for example, for choosing as the preferred head posture one of the recorded postures in which the subject keeps their head during near-range viewing and/or during far-range viewing.

Furthermore, it is expedient to take account of the body posture of the subject. A person will more likely be standing during far-range viewing, whereas a person preferably adopts a sitting position during near-range viewing, such as, for example, when reading. Therefore, the invention provides for choosing, as the preferred head posture, one of the recorded postures during which the subject is standing and/or sitting.

The habitual head posture is especially dependent on the subject's activity and the visual impressions perceived by the subject. It is therefore furthermore expedient to present the subject with specific everyday situations and/or everyday vision tasks from and on which the subject's habitual head posture is intended to be determined. The advantage associated therewith is that the subject/customer is diverted from the actual measurement situation and therefore does not adopt an unnatural head posture. The vision tasks may consist in the subject/customer moving freely, for example, in the store of the optician who records the habitual head posture and, for example, viewing the goods on display, or the subject/customer, for example, following traffic situations represented by means of an electronic medium, such as a display, a beamer, et cetera, as is described, for example, in United States patent application publication 2007/0229761 A1, or the subject/customer being requested to read through a piece of text. The vision tasks are chosen, for example, such that a typical head posture when standing and/or when sitting can be determined. During centering data determination for reading spectacles, it will be necessary to take into consideration, for example, the habitual head posture during which the subject is sitting and reading.

Specifically, the subject/customer, for the purpose of dynamically determining the habitual head posture over a time interval, can be presented with everyday situations or everyday vision tasks in the near and/or far range. In this time, the head posture, if appropriate in combination with the associated body posture and, if appropriate, also the (relative) positions such as, for example, the inclination of the spectacles or of the spectacle lenses worn by the subject, are measured continuously. The measurement is effected in such a way that the subject/customer is not adversely affected thereby. After the measurement, the respective most frequent head posture, and insofar as concomitantly recorded also the associated body posture, and, if appropriate, also the position, in particular inclination of the spectacles or of the spectacle lenses, can be determined and taken into account later when determining the centering data. In particular, it is possible to determine the viewing points during near- and/or distant-vision tasks, the so-called inset and/or the corridor length. Specifically, the viewing point through the spectacle lens can be determined, for example, from the head posture during viewing in the near and far range given a known position of the visual target. If the viewing points are known, it is thus also possible to determine the size of the inset, and also the length of the corridor of the near portion. A possible difference between head direction and viewing direction can also be taken into account when determining the viewing points and/or the inset.

The head posture of the subject can be determined in a wide variety of ways. Thus, by way of example, the recording of the head posture can be carried out by means of a position recording device fitted to the subject's head. The position recording device can be fixed indirectly, that is, for example, to the spectacle frame arm, or directly to the client's head. The position recording device can function according to the principle of a data logger with subsequent data transfer via a base station, or the data transfer can be effected simultaneously via a wireless connection, such as WPAN (Wireless Personal Area Network), namely, for example, via Bluetooth, or WLAN (Wireless Local Area Network), online during the entire measurement interval. The position recording device can measure either absolute position information or else changes in position. In the second case, the measured-value pick-up has to be brought to a reference position before and/or after the measuring process, the orientation of the reference position being known. By way of example, a horizontal table surface or the support of a mount provided specifically for this purpose can serve as the reference position.

The recording of the head posture can additionally or alternatively be carried out by means of an image recording device. An image recording device of this type can be e.g. a video or digital camera system with connected automated image evaluation. The image data can be processed further either as two-dimensional (2D) data directly or after the creation of a three-dimensional (3D) model as 3D data. By way of example, typical parameters such as forward inclination, lateral inclination, et cetera of the spectacles can also be determined from these data.

In the method according to the invention for determining centering data, the actual instantaneous head posture determined can be corrected with the aid of the habitual head posture determined in such a way that the centering data are determined on the basis of the habitual rather than the random head posture. The correction can be effected, for example, by determining the deviation of the instantaneous head posture from the habitual head posture and converting/correcting the centering values on the basis of this deviation.

The determined habitual head posture of the subject/customer and the forward inclination angle of the spectacles that is likewise determined, if appropriate, can also serve for the forced orientation of the customer for conventional centering data determination, by virtue of the fact that when the sought forward inclination angle of the spectacles is attained, an automatic triggering of the imaging units is initiated or a signal is given to the operator that the centering data can now be determined.

The invention also provides, in particular, for the above-described methods for determining the habitual head posture and for determining centering data to be present in the form of computer programs comprising program codes which are executable in a computer. The computer programs can be stored on a machine-readable data carrier.

For the sake of completeness, it is pointed out that the abovementioned recording device for recording the head posture over a period of time can comprise a position recording device and/or an image recording device which can be fitted to the subject's head. The position recording device and/or image recording device can be embodied, for example, in the manner described above. The determining device for determining a preferred head posture from the recording can comprise a computer.

The head posture determining device for determining the actual instantaneous head posture of a subject can comprise a position recording device and/or an image recording device, in particular of the type described above.

The determining device for determining the arrangement of a spectacle frame relative to the actual instantaneous head posture determined can comprise an image recording device, in particular a video or digital camera, and/or a computer.

BRIEF DESCRIPTION OF THE DRAWINGS

The invention will now be described with reference to the drawings wherein:

FIG. 2b shows a side view of the customer of FIG. 2a;

DESCRIPTION OF THE PREFERRED
EMBODIMENTS OF THE INVENTION

It is assumed that a customer visits an optician's store for the purpose of procuring a new pair of spectacles. Firstly, the customer is given advice with regard to the spectacle lenses and frames appropriate for the customer. After the frame has been selected, the actual centering data determination takes place with the aid of an apparatus according to the invention.

Figure 1:
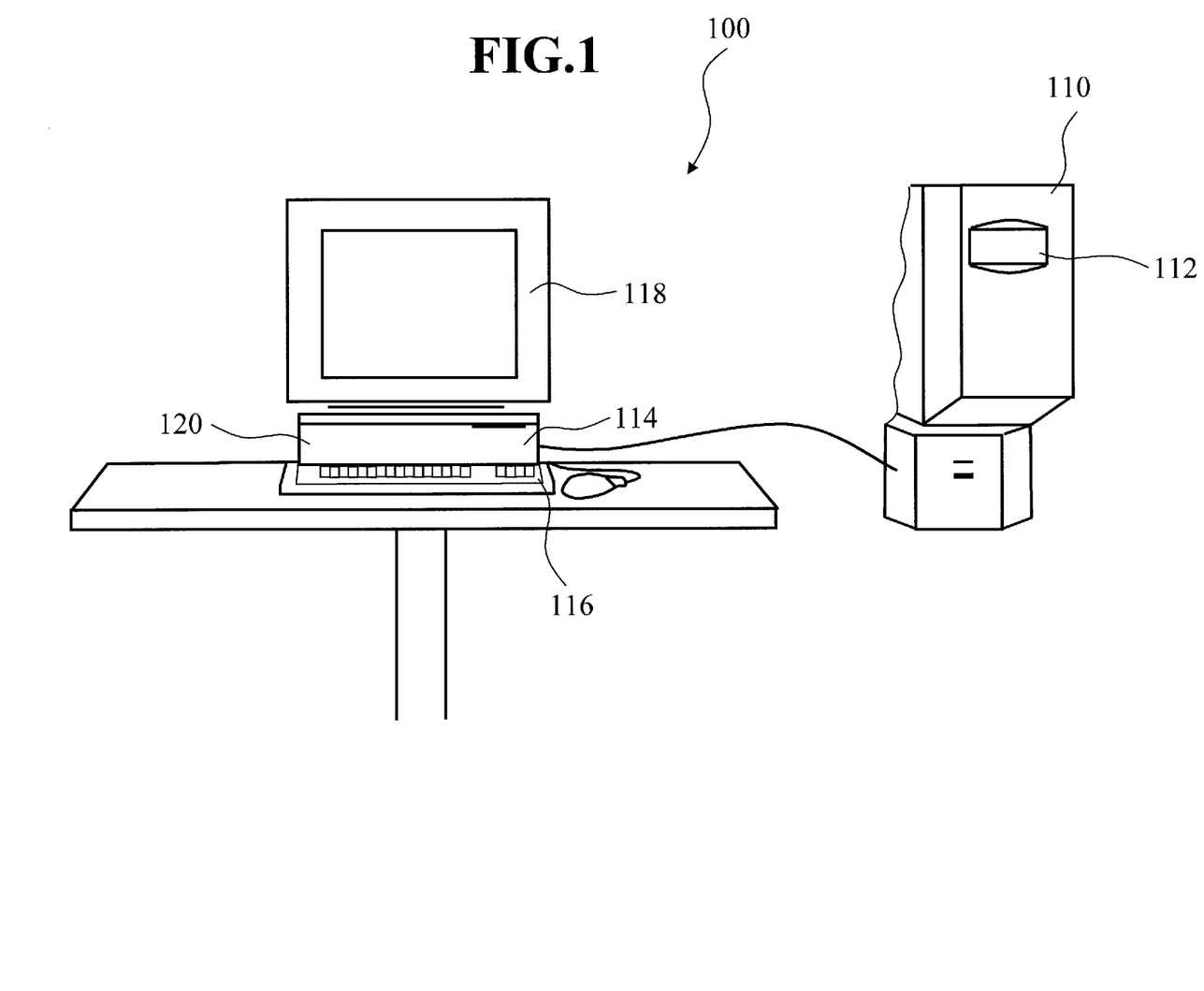
FIG. 1 shows a schematic of an apparatus according to the invention for determining centering data with a device according to the invention for determining the habitual head posture of a subject or customer.

FIG. 1 shows an apparatus according to the invention for determining centering data 100. This apparatus for determining centering data 100 comprises a video centering device 110 with video camera 112 and computer 114 with keyboard 116, screen 118 and storage medium 120. This is a calibrated system, that is, a system for recording and determining dimensions.

Figure 2A:
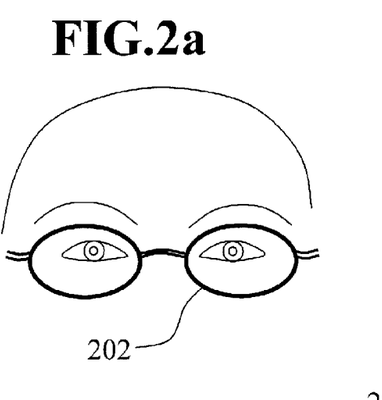
FIG. 2a shows a front view recording of the face of a customer with an adapted frame in the zero viewing direction.
Figure 2B:
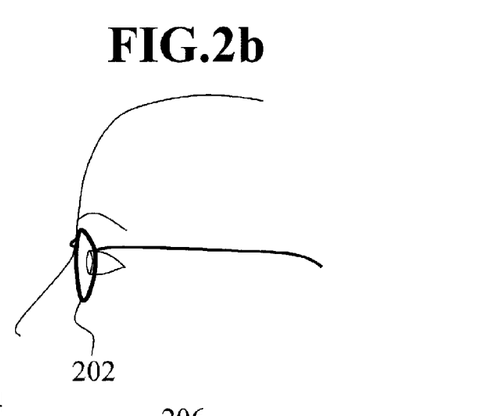

The customer's face is recorded with an adaptive frame 202 in the zero viewing direction from the front and from the side by means of the video camera 112, as is illustrated in FIGS. 2a and 2b.

With the front recording (FIG. 2c) represented on the screen 118, firstly the frame form 202 is detected. Furthermore, the pupil centers 204 are determined, for example, by the coincidence method, relative to the frame form 202. With the side recording, the corneal vertex distance HSA and the forward inclination (p) of the frame are determined in order to fulfill the eye rotation point requirement, as illustrated in FIG. 2d.

The invention now provides for recording the habitual head posture and the inclination of the spectacles, for example, with the aid of the calibrated video camera over a relatively long time period, and for determining therefrom a habitual head posture and a preferred inclination of the spectacles.

Figure 2C:
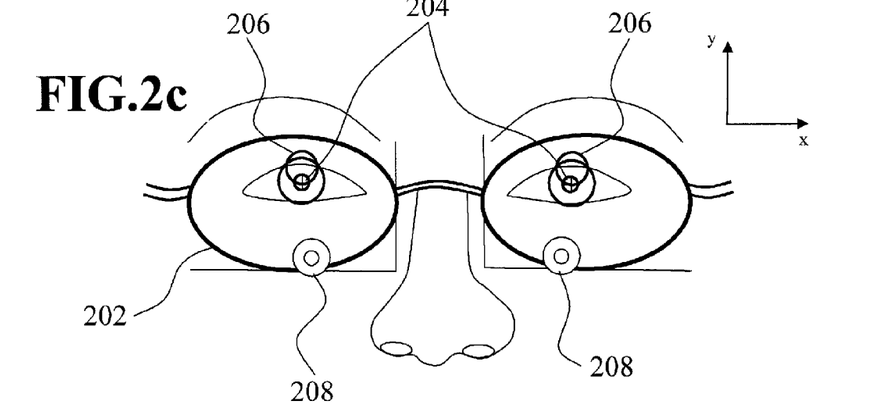
FIG. 2c shows a front view of the customer of FIG. 2a with centering data, namely (x, y); and, FIG. 2d shows a view from the side with centering data, namely corneal vertex distance and forward inclination of the frame.
Figure 2D:
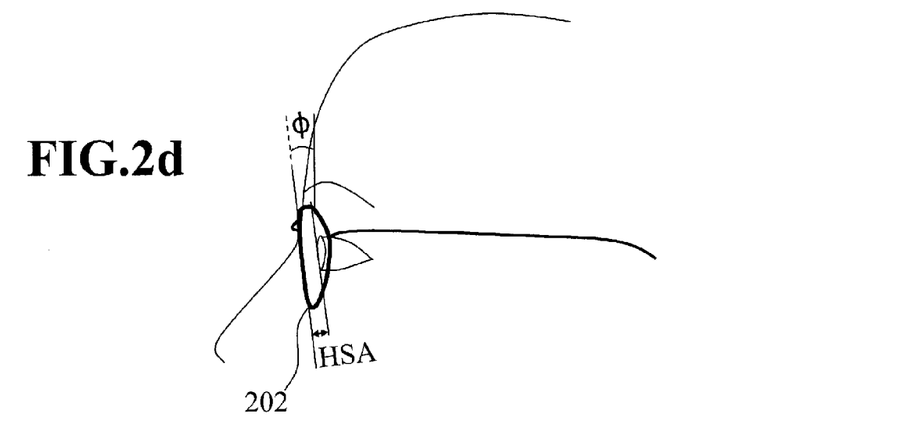

The head posture thus determined and the forward inclination angle of the spectacles associated therewith and also other measurement data serve for converting the centering data determined conventionally by means of the video centering device 110, if, during their determination, the customer had assumed a head posture deviating from the normal head posture (FIG. 2c). The other measurement data referred to above can, for example, be the arrangement of the spectacles in the frame or disc plane in (x, y). The centering data is, for example for reference point 206 and/or the near measurement circle 208.

It is understood that the foregoing description is that of the preferred embodiments of the invention and that various changes and modifications may be made thereto without departing from the spirit and scope of the invention as defined in the appended claims.

What is claimed is:

1. A method for dynamically determining the habitual head posture of a test person for whom spectacles are to be provided, the method comprising the steps of:
   with a recording device, recording the head posture of the test person over a time span during which the test person assumes a posture of the head by way of habit of the test person; and,
   with a determining device, determining a preferred or usual head posture of said test person from the recording of said head posture wherein the test person has assumed a head posture by way of habit unencumbered by any specific visual task assigned to the test person during recording of said head posture.

2. The method of claim 1, wherein said time span is a predetermined time span.

3. The method of claim 1, wherein a head posture is selected as said preferred head posture wherein said test person holds his/her head for a pregiven viewing task with a probability of over 20%.

4. The method of claim 3, wherein said probability is over 50%.

5. The method of claim 1, wherein the recorded posture is selected as said preferred head posture wherein said test person holds the head for a pregiven viewing task with the greatest probability.

6. The method of claim 1, wherein one of the recorded postures is selected as said preferred head posture wherein the test person holds the head with a close-in view and/or a far-out view.

7. The method of claim 1, one of the recorded postures being selected as said preferred head posture during which said test person stands and/or sits.

8. The method of claim 1, wherein said test person is offered everyday situations and/or everyday viewing tasks during which the test person assumes a natural head position via habit during the recording thereof.

9. The method of claim 1, further comprising the steps of:
   providing a position recording apparatus mounted on the head of the test person; and,
   carrying out the recording of the head posture by means of said position recording apparatus.

10. A method for determining centering data of a test person for whom spectacles are to be provided, the method comprising the steps of:
   (a) determining an actual instantaneous random head posture of the test person;
   (b) determining an arrangement of a spectacles frame relative to said specific actual instantaneous random head posture;
   (c) determining a habitual head posture with the aid of an automated process; and,
   (d) correcting the specific actual instantaneous random head posture with the aid of said habitual head posture;
   wherein said habitual head posture is determined by recording the head posture of the test person over a time span during which the test person assumes a posture of the head free of forced or unnatural head postures.

11. The method of claim 10, further comprising, in step (c), also determining the inclination (p) of said spectacles frame.

12. The method of claim 10, wherein said habitual head posture is determined by:
   determining a preferred or usual head posture of said test person from the recording of said head posture.

13. The method of claim 10, wherein the specific actual instantaneous head posture is so corrected with the aid of the specific habitual head posture that centering data ($\varphi$, HSA, x, y) is determined on the basis of the habitual head posture and not on the basis of a random head posture.

14. The method of claim 13, wherein the specific actual instantaneous head posture is corrected with the aid of the specific habitual head posture in that the deviation of the instantaneous head posture relative to the habitual head posture is determined and, on the basis of this deviation, a conversion of the centering values takes place.

15. A computer program stored on a non-transitory computer readable medium, comprising a program code for carrying out a method for determining the habitual head posture of a test person for whom spectacles are to be provided, the method comprising the steps of:
   recording the head posture of the test person over a time span during which the test person assumes a habitual posture of the head by way of habit of the test person; and,
   determining a preferred head posture of said test person from the recording of said head posture.

16. An apparatus for determining the habitual head posture of a test person for whom spectacles are to be provided, the apparatus comprising:
   a recording device for making a recording of the head posture over a time span during which the test person assumes a habitual posture of the head free of forced or unnatural head postures; and,
   a determining device for determining a preferred or usual head posture of said test person from said recording wherein the test person has assumed a head posture by way of habit unencumbered by any specific visual task assigned to the test person during recording of said head posture.

17. The apparatus of claim 16, wherein said recording device includes a position recording device mountable on the head of the test person and/or an image recording device.

18. The apparatus of claim 16, wherein said determining device includes a computer.

19. An apparatus for determining centering data of a test person for whom spectacles are to be provided, the apparatus comprising:

a head posture determining device for determining an actual instantaneous random head posture of the test person;

a determining device for determining an arrangement of a spectacles frame relative to the determined actual instantaneous random head posture;

a unit for automatically determining the habitual head posture; and, a correcting unit for correcting the determined actual instantaneous random head posture with the aid of the determined habitual head posture, wherein said habitual head posture is determined by recording the head posture of the test person over a time span during which the test person assumes a posture of the head free of forced or unnatural head postures.

20. The apparatus of claim 19, wherein said head posture determining device includes a position recording device and/or an image recording device.

21. The apparatus of claim 19, wherein said determining device includes an image recording device and/or a computer.

22. The apparatus of claim 19, wherein said unit for determining the habitual head posture is configured to include a recording device for making a recording of the head posture over a time span; and, a determining device for determining a preferred head posture from said recording.

23. A method for determining the habitual head posture of a test person for whom spectacles are to be provided, the method comprising the steps of:

recording the head posture of the test person over a time span during which the test person assumes a habitual posture of the head free of forced or unnatural head postures; and, determining a preferred head posture of said test person from the recording of said head posture, wherein it is left to the discretion of the test person in what body posture the test person views during the recording of his head posture and/or it is left to the discretion of the test person what the test person views during the recording of his head posture.

24. A computer program stored on a non-transitory computer readable medium, comprising a program code for carrying out a method for determining the habitual head posture of a test person for whom spectacles are to be provided, the method comprising the steps of:

recording the head posture of the test person over a time span during which the test person assumes a habitual posture of the head free of forced or unnatural head postures; and, determining a preferred head posture of said test person from the recording of said head posture wherein it is left to the discretion of the test person in what body posture the test person views during the recording of his head posture and/or it is left to the discretion of the test person what the test person views during the recording of his head posture.

25. An apparatus for determining the habitual head posture of a test person for whom spectacles are to be provided, the apparatus comprising:

a recording device for making a recording of the head posture over a time span during which the test person assumes a habitual posture of the head free of forced or unnatural head postures; and, a determining device for determining a preferred head posture from said recording of said head posture wherein it is left to the discretion of the test person in what body posture the test person views during the recording of his head posture and/or it is left to the discretion of the test person what the test person views during the recording of his head posture.

26. A method of determining centering data of a test person for whom spectacles are to be provided, the method comprising the steps of:

(a) determining an actual instantaneous random head posture of the test person;

(b) determining an arrangement of a spectacles frame relative to said specific actual instantaneous random head posture;

(c) determining a habitual head posture with the aid of an automated process; and, (d) correcting the specific actual random instantaneous head posture with the aid of said habitual head posture, wherein said habitual head posture is determined by recording the head posture of the test person over a time span during which the test person assumes a posture of the head free of forced or unnatural head postures, wherein the specific actual instantaneous random head posture is so corrected with the aid of said habitual head posture that said centering data are determined on the basis of said habitual head posture and not on the basis of said specific actual instantaneous random head posture.

27. An apparatus for determining centering data of a test person for whom spectacles are to be provided, the apparatus comprising:

a head posture determining device for determining an actual instantaneous random head posture of the test person wherein said habitual head posture is determined by recording the head posture of the test person over a time span during which the test person assumes a posture of the head free of forced or unnatural head postures;

a determining device for determining an arrangement of a spectacles frame relative to the specific determined actual instantaneous random head posture;

a unit for automatically determining the habitual head posture with aid of an automated process; and, a correcting unit for correcting the specific actual random instantaneous head posture with the aid of the determined habitual head posture, wherein the specific actual instantaneous random head posture is so corrected with the aid of said habitual head posture that said centering data are determined on the basis of said habitual head posture and not on the basis of said specific actual instantaneous random head posture.

28. A computer program stored on a non-transitory computer readable medium, comprising a program code for carrying out a method for determining centering data of a test person for whom spectacles are to be provided, the method comprising the steps of:

(a) determining an actual instantaneous random head posture of the test person;

(b) determining an arrangement of a spectacles frame relative to said specific actual instantaneous random head posture;

(c) determining a habitual head posture with the aid of an automated process; and, (d) correcting the specific actual random instantaneous head posture with the aid of said habitual head posture, wherein said habitual head posture is determined by recording the head posture of the test person over a time span during which the test person assume a posture of the head free of forced or unnatural head postures, wherein the specific actual instantaneous random head posture is so corrected with the aid of said habitual head posture that said centering data are determined on the basis of said habitual head posture and not on the basis of said specific actual instantaneous random head posture.

* * * * *

UNITED STATES PATENT AND TRADEMARK OFFICE
CERTIFICATE OF CORRECTION

PATENT NO. : 9,500,885 B2  
APPLICATION NO. : 13/329043  
DATED : November 22, 2016  
INVENTOR(S) : M. Kubitza et al.

Page 1 of 1

It is certified that error appears in the above-identified patent and that said Letters Patent is hereby corrected as shown below:

In the Specification

In Column 7:
Line 1: delete "(p)" and substitute -- (φ) -- therefor.

In the Claims

In Column 8:
Line 19: delete "(p)" and substitute -- (φ) -- therefor.
Line 27: delete "ϕ" and substitute -- φ -- therefor.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*